United States Patent [19]

Findeisen

[11] 4,432,910
[45] Feb. 21, 1984

[54] PREPARATION OF PIVALOYL CYANIDE

[75] Inventor: Kurt Findeisen, Odenthal, Fed. Rep. of Germany

[73] Assignee: Bayer Aktiengesellschaft, Leverkusen, Fed. Rep. of Germany

[21] Appl. No.: 320,042

[22] Filed: Nov. 10, 1981

[30] Foreign Application Priority Data

Dec. 1, 1980 [DE] Fed. Rep. of Germany ....... 3045181

[51] Int. Cl.$^3$ .......................................... C07C 120/00
[52] U.S. Cl. ............................. 260/545 R; 260/465.1
[58] Field of Search ......................... 260/465.1, 545 R

[56] References Cited

U.S. PATENT DOCUMENTS

| 4,108,875 | 8/1978 | Klenk et al. ............... 260/545 R X |
| 4,108,877 | 8/1978 | Klenk et al. ............... 260/545 R X |
| 4,122,116 | 10/1978 | Klenk et al. ................... 260/545 R |
| 4,238,412 | 12/1980 | Findeisen et al. ............. 260/545 R |
| 4,284,584 | 8/1981 | Findeisen ........................ 260/545 R |

FOREIGN PATENT DOCUMENTS

| 2614241 | 2/1976 | Fed. Rep. of Germany . |
| 2708182 | 8/1978 | Fed. Rep. of Germany . |
| 2708183 | 8/1978 | Fed. Rep. of Germany . |
| 2660344 | 8/1980 | Fed. Rep. of Germany . |

OTHER PUBLICATIONS

Angewandte Chemie 68, pp. 425-435, (1956), Thesino, et al.

Primary Examiner—Joseph Paul Brust
Attorney, Agent, or Firm—Sprung, Horn, Kramer & Woods

[57] ABSTRACT

In the preparation of pivaloyl cyanide of the formula $(CH_3)_3C—CO—CN$ by reaction of pivalic acid anhydride with anhydrous hydrocyanic acid, the improvement which comprises carrying out the reaction continuously in the presence of a catalyst comprising an alkali metal/copper cyanide complex, an alkaline earth metal/copper cyanide complex or an alkali metal salt, or an alkaline earth metal salt, of an aliphatic, cycloalkphatic or aromatic, carboxylic acid, or a precursor of such a salt, in either case optionally in admixture with a Lewis acid, and in the presence of an inert, aprotic organic diluent, which boils above about 210° C., at a temperature between about 180° and 240° C., by simultaneously and continuously dropping the pivalic acid anhydride and introducing the hydrocyanic acid in gaseous form into a stirred suspension of the catalyst in the diluent, and continuously distilling the crude product mixture consisting essentially of pivaloyl cyanide, pivalic acid and unreacted hydrocyanic acid, the unreacted hydrocyanic acid being separated off by evaporation and being recycled to the reaction vessel, and the pivaloyl cyanide being separated from the precipitated crude product mixture by fractional distillation in vacuo. Advantageously the reaction is carried out at a temperature between about 195° and 225° C., the complex cyanide of the formula $Na_3[Cu(CN)_4]$, $K_3[Cu(CN)_4]$, $Ca_3[Cu(CN)_4]_2$ or $Ba_3[Cu(CN)_4]_2$ is employed as the catalyst, diphenyl ether is employed as the diluent, and about 1 to 2 moles of pivalic acid anhydride and about 5 to 8 moles of hydrocyanic acid are introduced into the suspension of catalyst per hour.

7 Claims, No Drawings

PREPARATION OF PIVALOYL CYANIDE

The invention relates to an unobvious process for the preparation of pivaloyl cyanide.

Pivaloyl cyanide can be used as an intermediate product for the preparation of known herbicidal active compounds.

It has already been disclosed that pivaloyl cyanide can be obtained by heating pivalic acid anhydride with anhydrous hydrocyanic acid in an autoclave for several hours to 250° C., and fractionally distilling the reaction mixture obtained; the yield is 88% of theory in a 5 mol reaction mixture (see German Patent Specification No. 2,614,241, Example 4). However, in order to achieve this result, it is necessary to carry out individual reactions in the autoclave, and a development of this process as a continuous process would be associated with very considerable technical effort. In addition, it has been found that a reduction in the yield occurs with relatively large batches.

The present invention now provides a process for the preparation of pivaloyl cyanide, of the formula $$(CH_3)_3C-CO-CN \qquad (I),$$

in which pivalic acid anhydride, of the formula $$(CH_3)_3C-CO-O-CO-C(CH_3)_3,$$

is reacted with anhydrous hydrocyanic acid, the reaction being carried out in the presence of an alkali metal/copper cyanide complex or an alkaline earth metal/copper cyanide complex as catalyst, and in the presence of an inert, aprotic organic solvent, which boils above 210° C., as diluent, at a temperature between 180° and 240° C., and under normal pressure, in such a manner that, simultaneously and continuously, the pivalic acid anhydride is allowed to drop into, and the hydrocyanic acid is introduced in gaseous form into, a suspension of the catalyst in the diluent, which is stirred at the reaction temperature, and that the crude product mixture, consisting essentially of pivaloyl cyanide, pivalic acid and unreacted hydrocyanic acid, is continuously distilled off from the reaction vessel, the unreacted hydrocyanic acid is separated off by evaporation and is recycled into the reaction vessel, and the pivaloyl cyanide is separated from the precipitated crude product mixture by fractional distillation in vacuo.

The present invention permits the preparation of pivaloyl cyanide, in very high yield and purity, by a continuous procedure.

With regard to the known state of the art (Angewandte Chemie 68, pages 425–435 (1956)), it is surprising that the reaction of pivalic acid anhydride with hydrocyanic acid can be catalyzed by the basic complex salts mentioned, so that in comparison to the process previously known from German Patent Specification No. 2,614,241 (Example 4) (3 hours at 250° C. and appropriate elevated pressure in the autoclave), the reaction can be carried out at lower temperatures, with substantially shorted duration (of the order of a few minutes) and at normal pressure, and, simultaneously, higher yields are obtained and a throughput of large quantities is possible. In this process, it is surprising on the one hand that the discovered catalytic activity of the complex salts mentioned is, in principle, retained for an unlimited period of time, and that the salts thus do not react with pivalic acid anhydride to give pivaloates plus pivaloyl cyanide, and thereby become deactivated; on the other hand, it is surprising that, in spite of the presence of basic agents, no dimeric pivaloyl cyanide is formed, and that the hydrocyanic acid does not polymerize. In addition, the finding that other lower aliphatic carboxylic acid anhydrides can be reacted in a corresponding manner only with substantially lower yields is particularly surprising.

The course of the reaction can be represented by the following equation:

$$(CH_3)_3C-CO-O-CO-C(CH_3)_3 + HCN \xrightarrow[\text{diluent}]{\text{180-240° C.}\atop\text{catalyst}}$$

$$(CH_3)_3C-COOH + (CH_3)_3C-CO-CN$$

It has been found that, instead of pivalic acid anhydride, the equivalent quantity of pivaloyl chloride can also be employed. In this case, hydrogen chloride is liberated instead of pivalic acid, and the former must be removed in a suitable manner.

The reaction according to the invention is carried out in the presence of an alkali metal/copper cyanide complex or alkaline earth metal/copper cyanide complex as catalyst. Such complex compounds are formed by reaction of alkali metal and alkaline earth metal cyanides with copper-(I) cyanide. The formation of sodium copper cyanide (sodium tetracyanocuprate-(I)), is given as an example:

$$3NaCN + CuCN \rightarrow Na_3[Cu(CN)_4].$$

Further examples of suitable complex compounds of this type are $K_3[Cu(CN)_4]$, $Ca_3[Cu(CN)_4]_2$ and $Ba_3[Cu(CN)_4]_2$.

It is particularly appropriate freshly to prepare the complex compound to be used as catalyst, from the individual components, in the reactor before the beginning of the continuous reaction.

It has further been found that certain basic-reacting salts, which are not volatile under the reaction conditions, can also be used as the catalyst, if appropriate in combination with certain Lewis acids. Examples of salts of this type which may be mentioned are the sodium, potassium, lithium, calcium, strontium and barium salts of aliphatic, cycloaliphatic and aromatic carboxylic acids. Sodium and potassium pivaloate are preferred salts of this type. Instead of these salts, compounds can also be used which can be easily converted into the salts mentioned, for example hydroxides, alcoholates, cyanides and carbonates of sodium, potassium, lithium, calcium, strontium and barium, and the like. Zinc chloride, zinc cyanide, copper-(I) cyanide, copper-(II) cyanide, copper oxide and metallic copper may be mentioned as suitable Lewis acids.

The ratio of the Lewis acid to the basic-reacting salt should preferably be chosen so that the complex formed is likewise basic.

The catalysts mentioned are of long duration and regenerate themselves during the reaction. A decline in the activity of the catalysts has not previously been observed in any instance.

In addition, the reaction according to the invention is carried out in the presence of an inert, aprotic organic solvent, which boils above 210° C., as the diluent. Examples of diluents of this type which may be mentioned are diphenyl ether, 1,3,5-triisopropylbenzene, 1,2,4-trichlorobenzene, propyl benzoate and 2,3,4-trichlorotoluene. Diphenyl ether is preferably used.

The reaction temperature can be varied in a relatively large range. In general, the reaction is carried out, as given above, at a temperature between 180° and 240° C., preferably at between 195° and 225° C.

It has proved to be expedient to employ about 0.1 to 0.2 mole of the catalyst per liter of diluent in carrying out the process. Under these conditions, about 1 to 2 moles of pivalic acid anhydride per hour and excess hydrocyanic acid (for example 5 to 8 moles per hour) can be introduced up to 90% of the pivalic acid anhydride being converted. The excess, unreacted hydrocyanic acid is recycled into a reserve vessel and finally into the reactor.

The product mixture, which consists of equivalent amounts of pivaloyl cyanide (I) and pivalic acid, is continuously distilled off from the reactor; in this process, the unreacted hydrocyanic acid, as well as small amounts of unreacted pivalic acid anhydride (<10%) and, if appropriate, of diluent, pass over with the product mixture.

Firstly, the hydrocyanic acid is separated off by evaporation and, as already described, recycled. The pivaloyl cyanide (I) and the remaining constituents of the crude distillate are then separated by fractional distillation and isolated and, if necessary, further processed.

The pivaloyl cyanide of the formula (I), which can be prepared according to the process according to the invention, is a valuable starting material, for example for the synthesis of 1,2,4-triazin-5-ones, which have excellent herbicidal properties (see, for example, German Patent Specification No. 1,795,784). Thus, for example, pivaloyl cyanide can be converted into the herbicidally active compound 3-methylthio-4-amino-6-tert.-butyl-1,2,4-triazin-5-one by the following reaction sequence:

Acid hydrolysis (see Angew. Chem. 68, page 430 (1956)), reaction of the α-ketoacid formed (3,3-dimethyl-2-oxobutyric acid) with thiocarbohydrazide (see Chem. Ber. 97, pages 2173-8 (1964)) and methylation of the 3-mercapto-4-amino-6-tert.-butyl-1,2,4-triazin-5-one formed, for example by means of methyl bromide (see DE-OS (German Published Specification) No. 2,729,761); see also DE-OS No. 3,003,541.

The example which follows is intended to illustrate the process according to the invention:

EXAMPLE 1

Arrangement of the experiment:

The reaction was carried out in a 2 liter four-necked flask which was heated with oil. The flask had the following attachments: stirrer, inlet capillary (for hydrocyanic acid; connected via a pre-evaporator and a dosing pump to a hydrocyanic acid reserve vessel), dropping funnel (for pivalic acid anhydride), thermometer and a silver-jacketed column, filled with Raschig rings, with a column head. A condenser was connected to the column head, and this condenser discharged into a further four-necked flask stirring apparatus of the same size, which was provided with an outlet in the base. This second flask was maintained at 90° to 95° C. A column charged with warm water (30° C.), on which there was a distillation bridge cooled with cooling brine, was situated at a side neck of the second flask. The unreacted hydrocyanic acid was condensed in the bridge and recycled into the reserve vessel. The hydrocyanic acid was pumped with a cooled dosing pump via a pre-evaporator and through the capillary mentioned above into the reaction vessel.

Execution of the experiment:

600 ml of diphenyl ether and—to produce the catalyst $Na_3[Cu(CN)_4]$—8.9 g (0.1 mol) of copper-(I) cyanide and 15 g (0.3 mol) of 98% strength sodium cyanide were initially introduced into the reactor (2 liter four-necked flask). Hydrocyanic acid was introduced via the dosing pump, pre-evaporator and inlet capillary, at the reaction temperature of from 205° to 215° C. (about 250 to 300 ml (6.5 to 7.5 mol) of HCN per hour). About 250 to 280 g (1.35 to 1.5 mol) per hour of pivalic acid anhydride were dropped into the mixture from the reserve vessel dropping funnel for pivalic acid anhydride. The products leaving the reaction vessel and the excess hydrocyanic acid were adjusted to a temperature of 110° to 115° C. in the column head. The excess hydrocyanic acid was expelled in the connected four-necked flask with an outlet in the base, and was collected in the reserve vessel.

The reaction product was removed via the outlet in the base, and was distilled.

2,536 g (13.63 mol) of pivalic acid anhydride were added dropwise to the reaction mixture in the course of 10 hours.

Collected quantity of crude distillate (after 10 hours): 3,082 g.

The crude distillate was distilled over a silver-jacketed column with filling material, which had a column head positioned on top, to separate the reaction products.

Yield: 1,442 g of pivaloyl cyanide (=95.3% of theory); boiling point: 53°–55° C./130–140 mbars.

In addition, the following had been obtained: 1,316 g of pivalic acid (=94.7% of theory), boiling point: 163° C. or 70° C./18.6 mbars; 154 g of pivalic acid anhydride (approximately 6%, unreacted), boiling point: 190° C.; 120 g of diphenyl ether, boiling point: 252° C. or 127° C./13.3 mbars.

It will be appreciated that the instant specification and examples are set forth by way of illustration and not limitation, and that various modifications and changes may be made without departing from the spirit and scope of the present invention.

I claim:

1. In the preparation of pivaloyl cyanide of the formula

$(CH_3)_3C-CO-CN$ by reaction of pivalic acid anhydride with anhydrous hydrocyanic acid, the improvement which consists essentially of carrying out the reaction continuously in the presence of a catalyst comprising an alkali metal/copper cyanide complex or an alkaline earth metal/copper cyanide complex, and in the presence of an inert, aprotic organic diluent, which boils above about 210° C., at a temperature between about 180° and 240° C., by simultaneously and continuously dropping the pivalic acid anhydride and introducing the hydrocyanic acid in gaseous form into a stirred suspension of the catalyst in the diluent, and continuously distilling the crude product mixture consisting essentially of pivaloyl cyanide, pivalic acid and unreacted hydrocyanic acid, the unreacted hydrocyanic acid being separated off by evaporation and being recycled to the reaction vessel, and the pivaloyl cyanide being separated from the precipitated crude product mixture by fractional distillation in vacuo.

2. A process according to claim 1, wherein the reaction is carried out at a temperature between about 195° and 225° C.

3. A process according to claim 1, wherein the complex cyanide of the formula $Na_3[Cu(CN)_4]$, $K_3[Cu(CN)_4]$, $Ca_3[Cu(CN)_4]_2$ or $Ba_3[Cu(CN)_4]_2$ is employed as the catalyst.

4. A process according to claim 1, wherein diphenyl ether is employed as the diluent.

5. A process according to claim 1, wherein about 0.1 to 0.2 mole of catalyst is employed per liter of diluent.

6. A process according to claim 1, wherein about 1 to 2 moles of pivalic acid anhydride and about 5 to 8 moles of hydrocyanic acid are introduced into the suspension of catalyst per hour.

7. A process according to claim 6, wherein the reaction is carried out at a temperature between about 195° and 225° C., the complex cyanide of the formula $Na_3[Cu(CN)_4]$, $K_3[Cu(CN)_4]$, $Ca_3[Cu(CN)_4]_2$ or $Ba_3[Cu(CN)_4]_2$ is employed as the catalyst, diphenyl ether is employed as the diluent and about 0.1 to 0.2 moles of catalyst is employed per liter of diluent.

* * * * *